(12) United States Patent
Urban et al.

(10) Patent No.: US 12,376,996 B2
(45) Date of Patent: Aug. 5, 2025

(54) HEARING PROTECTOR WITH SENSOR MODULE AND METHOD OF RETROFITTING A HEARING PROTECTOR WITH A SENSOR MODULE

(71) Applicant: 3M INNOVATIVE PROPERTIES COMPANY, St. Paul, MN (US)

(72) Inventors: Henning T. Urban, Kuehlungsborn (DE); Jonas A. Nilsson, Värnamo (SE); Abel Gladstone Mangam, Värnamo (SE); Caroline M. Ylitalo, Stillwater, MN (US); William Bedingham, Woodbury, MN (US); Erik O. Levholt, Ödeshög (SE); Patrick R. T. Hjort, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 139 days.

(21) Appl. No.: 18/258,219

(22) PCT Filed: Dec. 20, 2021

(86) PCT No.: PCT/IB2021/062039
§ 371 (c)(1),
(2) Date: Jun. 19, 2023

(87) PCT Pub. No.: WO2022/137091
PCT Pub. Date: Jun. 30, 2022

(65) Prior Publication Data
US 2024/0293261 A1  Sep. 5, 2024

(30) Foreign Application Priority Data
Dec. 23, 2020 (EP) .................................... 20217115

(51) Int. Cl.
*H04R 29/00* (2006.01)
*A61F 11/14* (2006.01)

(52) U.S. Cl.
CPC ..... *A61F 11/145* (2022.01); *A61F 2230/0065* (2013.01)

(58) Field of Classification Search
CPC ..................................................... A61F 11/145
(Continued)

(56) References Cited

U.S. PATENT DOCUMENTS

| 9,232,292 B2 * | 1/2016 | Haapapuro | ............ H04R 1/086 |
| 2006/0140416 A1 * | 6/2006 | Berg | ....................... A61F 11/12 |
| | | | 381/72 |

(Continued)

FOREIGN PATENT DOCUMENTS

| CN | 102613963 A | 8/2012 |
| CN | 208675489 U | 3/2019 |

(Continued)

OTHER PUBLICATIONS

Extended European Search Report received for EP Application No. 20217115.3, mailed on Jun. 11, 2021, 2 pages.

(Continued)

*Primary Examiner* — William J Deane, Jr.

(57) ABSTRACT

The present disclosure relates to a hearing protector (10) with a sensor module (30) having a module sensor (32). The sensor module (30) is removably attached to the cushion (22, 24) and the cup (12A, 14A) of the earmuff (12, 14) of the hearing protector (10). The hearing protector (10) according to present disclosure allows the arrangement of sensors at a hearing protector (10) in an easy and cost-efficient way even with multiple sensors. The advantage of such a hearing protector (10) is an easy, compact and reliable solution of a hearing protector (10) providing information about the envi- (Continued)

ronment and about the conditions of the user (100) or worker using such a hearing protector (10). Also, a method of retrofitting such a sensor module (30) to a hearing protector (1) is provided. Such a method is advantageous because reversible retrofitting of existing hearing protectors (1) not having the required functionality of sensors is provided.

15 Claims, 4 Drawing Sheets

(58) Field of Classification Search
USPC .................................................. 381/72, 74
See application file for complete search history.

(56) References Cited

U.S. PATENT DOCUMENTS

| | | | | |
|---|---|---|---|---|
| 2017/0142530 | A1* | 5/2017 | Neumeyer | H04R 25/30 |
| 2018/0303392 | A1 | 10/2018 | Everman et al. | |
| 2018/0310893 | A1 | 11/2018 | Everman et al. | |
| 2019/0110929 | A1* | 4/2019 | Persson | H04R 1/1041 |
| 2020/0368071 | A1* | 11/2020 | Kara | H04R 1/288 |
| 2020/0396532 | A1* | 12/2020 | Bui | H04R 1/1083 |
| 2023/0072510 | A1* | 3/2023 | Górová | H04R 1/1083 |
| 2023/0114196 | A1* | 4/2023 | Reibner | H04M 1/6066 |
| | | | | 455/518 |
| 2024/0041147 | A1* | 2/2024 | Johansson | A61F 11/145 |
| 2024/0121577 | A1* | 4/2024 | Mangam | H04W 4/50 |
| 2024/0180750 | A1* | 6/2024 | McIntosh | H04R 1/1041 |

FOREIGN PATENT DOCUMENTS

| | | |
|---|---|---|
| CN | 209057342 U | 7/2019 |
| KR | 20170100931 A | 9/2017 |
| WO | 2016075270 A1 | 5/2016 |
| WO | 2018002883 A1 | 1/2018 |
| WO | 2019051270 A1 | 3/2019 |
| WO | 2019104172 A1 | 5/2019 |

OTHER PUBLICATIONS

International Search Report received for PCT International Application No. PCT/IB2021/062039, mailed on Mar. 31, 2022, 5 pages.

* cited by examiner

HEARING PROTECTOR WITH SENSOR MODULE AND METHOD OF RETROFITTING A HEARING PROTECTOR WITH A SENSOR MODULE

CROSS REFERENCE TO RELATED APPLICATIONS

This application is a national stage filing under 35 U.S.C. 371 of PCT/IB2021/062039, filed Dec. 20, 2021, which claims the benefit of EP Application Serial No. 20217115.3, filed Dec. 23, 2020, the disclosure of which is incorporated by reference in its/their entirety herein.

The present disclosure relates to a hearing protector with a sensor module. The present disclosure also relates to a method of retrofitting a hearing protector with a sensor module.

Hearing protectors as personal protection equipment (PPE) are typically used in noisy environments for protecting a wearer's hearing from noise at potentially harmful noise levels. Typically, hearing protectors have two muffs or caps which cover the ears of the wearer and which are connected to one another by a headband. Each cup further typically is formed by a rigid shell that is furnished with a noise dampening material, for example a foamed material.

There is a general desire to make hearing protectors user-friendly, in particular to encourage persons that are in noisy environments for longer times to actually wear the protectors. While noise dampening is the essential purpose of a hearing protector, there is often a need for the wearer to know about conditions of the environment the worker is in.

For example, the ambient temperature, humidity, pressure as well as ambient sound may be a relevant information for the worker. Furthermore, also conditions of the worker may be important to know, e. g. physiological parameters or movement of the worker. In some instances, such information may be required from a safety perspective or required to have because of regulatory aspects.

With the increasing trend towards digitization across all aspects of life it is becoming an imperative that needs to be reflected in the PPE space. There is a growing expectation that the workforce becomes more digitally aware more and more. For example, US 2018/0310893 A1 describes systems and methods or measuring physiological parameters, wherein sensors are attached to the housing or the cup of a headset. Another example is described in WO 2019/051270 A1, where a sensor is mounted via a sensor mount to the cushion of a headset.

This leads to a complex arrangement of multiple sensors necessary to gather the required or desired information. The main design challenge for implementing these technologies into hearing protectors is twofold. Firstly to find an implementation that is cost effective within the price range of the product portfolio and secondly to minimize the size and weight of electronic circuit board with sensors, processor, power supply, and wireless transmitter so that they fit into the confined space of the hearing protector without impairing the user's comfort levels, such as force on the head, weight, compatibility with other PPE etc.

Although existing solutions may to some extent provide the necessary data through the arrangement of sensors, there is still a need to provide an easy and cost-effective solution to equip a hearing protection device with the required sensors. It is therefore an object of the present disclosure to provide an easy and cost-effective solution of a hearing protector with multiple sensors. It is also an object of the present disclosure to equip existing hearing protection devices with the required multiple sensor.

The present disclosure relates to a hearing protector comprising two earmuffs. Preferably, the earmuffs are generally dome-shaped. Each earmuff has a first side facing—in use—towards an ear of a user and a second side opposite to each other. The earmuffs each comprise a cup comprising a first side and a second side opposite to each other. The earmuffs each comprise a cushion comprising a first side and a second side opposite to each other, and at least one cushion sensor. At least one of the earmuffs further comprises a sensor module comprising a first side and a second side opposite to each other and at least one module sensor. The sensor module is removably attached with its second side to the first side of the cup. The sensor module is removably attached with its first side to the second side of the cushion and the sensor module is connected to the at least one cushion sensor. Such a hearing protector is advantageous as it provides for an easy, compact and reliable solution of a hearing protector providing information about the environment and about the condition of the worker using such a hearing protector. In particular, the arrangement of multiple sensors in the cushion as well as in a sensor module is beneficial because different information can be gathered in a reliable way.

Furthermore, the present disclosure relates to a method of retrofitting a hearing protector with a sensor module according to the present disclosure. The method comprising the step of providing a hearing protector comprising two earmuffs, each earmuff having a first side facing—in use—towards an ear of a user and a second side opposite to each other, wherein the earmuffs each comprise a cup comprising a first side and a second side opposite to each other and a cushion comprising a first side and a second side opposite to each other and at least one cushion sensor. Preferably, the earmuffs are generally dome-shaped. The method further comprises the steps of providing a sensor module comprising a first side and a second side opposite to each other and at least one module sensor, wherein the sensor module is configured to be removably attached with its second side to the first side of the cup, wherein the sensor module is configured to be removably attached with its first side to the second side of the cushion and wherein the sensor module is configured to be connected to the at least one cushion sensor, detaching the cushion from the cup, attaching the sensor module with its second side to the first side of the cup and attaching the sensor module with its first side to the second side of the cushion. Such a method is advantageous because reversible retrofitting of existing hearing protectors not having the required functionality of sensors is provided. The reversible retrofitting of a sensor module further allows to easily change the sensor configuration according to different needs of the user of such hearing protectors. Furthermore, retrofitting of existing hearing protectors helps to increase functionality of these without the need to obtain new hearing protectors, if multiple sensors are needed and/or if different sensors are needed. Also, waste of material may thereby be minimized or avoided.

Hearing protectors typically have two muffs or caps which cover the ears of the wearer and which are connected to one another by a headband. Each cup further typically is formed by a rigid shell that is furnished with a noise dampening material, for example a foamed material. Each cup has an ear-facing side, which—in use—faces towards the ear of a user and a closed side, which faces away from the user's ear. Typically, materials for the cushion comprise a porous or foamed material. Alternatively, the materials comprise a non-porous or foam-free material, e. g. silicone material of a theoretical density of between 1.1 g/cm³ and 1.2 g/cm³. The material and the structure of the cushion typically provide for resilient properties, allowing the cushion to adapt tightly and sealingly with a user's or wearer's skin. It is also conceivable to include rubber as material for the cushion. The cushion may be cut-off or molded to achieve the desired size and shape.

Sensors suitable for the hearing protector according to the present disclosure comprise cushion sensors for sensing conditions of the cushion of the skin contacted by the cushion, cup sensors for sensing conditions of the cup, skin sensors for sensing skin conditions of a user or wearer, physiological sensors for sensing physiological parameters of a user or wearer, environmental sensors for sensing environmental or ambient conditions of the surrounding of a user or wearer and/or movement sensors for sensing a movement of a user or wearer.

A sensor module within the meaning of the present disclosure is understood as a module which comprises at least one sensor. Besides the at least one sensor, it comprises electronic components such as, e. g. processing units for processing sensor data, transmission units for transmitting and/or receiving sensor data from and/or to other devices for further processing of such data and optionally a power supply. In some embodiments, the sensor module is a self-contained module having attachment means for attaching the sensor module to a cushion and a cup of a hearing protector, respectively.

Connections between components or units of the hearing protector, e. g. between the sensor module and its components, individual sensor inside or outside of the sensor module to each other, or other components such as microphones, may, for example, be electrically or optically. The connection may be wired, e. g. electrical wires, optical fibers or wirelessly, e. g. of the type Radio frequency Identification (RFID), Bluetooth, Bluetooth Low Energy (BLE), ZigBee, Near Field Communication (NFC), Near Field Magnetic Induction (NFMI) or other suitable wireless connections. Also, light signals, e. g. Infrared Light signals, wirelessly sent are conceivable for such connections.

Attachment within the meaning of the present disclosure includes a removable attachment (i. e. being detachable after the initial attachment) and a non-removable attachment (i. e. being permanently fixed after the initial attachment). Attachment means are used for attachment, e. g. mechanical attachment means such as threads, screws, snap-fit, bayonet, mechanical fasteners like hook and loop systems. Alternatively, adhesive attachment means may be used, e. g. adhesives such as pressure sensitive adhesives or hotmelts. The selection of the attachment means may also depend on whether the attachment is removable or non-removable. Removable attachment means are rather mechanical attachment means, whereas non-removable attachment means rather comprise adhesive attachment means, rivets, bolts, soldering, welding or the like.

In one embodiment, the sensor module of the hearing protector further comprises a processing unit for processing a sensor signal from the module sensor and/or from the cushion sensor. The advantage of such a processing unit in the sensor module is that the processing occurs closely located to the sensors of the sensor module. Also, a compact design with the required functionality of the sensor module is achieved thereby. It is understood by the skilled person, that the processing unit uses software for the processing of the sensor signals including specific signal processing algorithms. Such a software may be provided initially on the processing unit. It is conceivable to transfer such software onto the processing unit later on and/or update such a software, e. g. via cloud-based services. The processing unit may require an interface and a transfer unit, respectively, for such an update.

In another embodiment, the cushion of the hearing protector is molded, wherein the cushion optionally comprises at least one opening. Such openings may go through the cushion material such that passages through the cushion are formed thereby. The advantage of such a molded cushion is that an easy and reliable manufacturing of the cushion is achieved thereby. In particular, forming openings and/or passages through the cushion can easily and reliably be achieved by a molding process. Suitable molding processes include injection molding, in particular a two shot-injection molding process which even allows to form more than one component at a time, if required. The advantage of openings and passages through the cushion is that these provide access to a cushion sensor, which is located within the cushion.

In a further embodiment, the cushion sensor of the hearing protector is spring-mounted to the cushion. Such a spring-mounting provides for an easy and reliable attachment of the sensor to the cushion. Also, spring-mounting may allow for a quick and easy change of the configuration of the sensor, i. e. removal or replacement of such a sensor.

In yet another embodiment, the sensor module of the hearing protector is ring-shaped. Such a ring-shape provides for a good fit of the sensor module to a cup and a cushion, respectively, of a hearing protector as these are typically ring-shaped. Also, a ring-shaped module may easily be provided with a threaded portion for attachment.

In still another embodiment, the sensor module of the hearing protector comprises a mounting ring being shaped and sized essentially in accordance to the shape and size of the cushion, wherein the mounting ring is adapted for carrying the cushion. Such a mounting ring provides for a good fit of the sensor module to a cup and a cushion, respectively, of a hearing protector as these are typically ring-shaped.

In a further embodiment, the mounting ring of the hearing protector has a first retention structure being retained with a corresponding second retention structure at the cup. For example, a retention structure may be provided as a connection means in the form of a thread or any other suitable connection means. Such a retention structure provides for an easy and reliable attachment of the sensor module to the cup and the cushion, respectively, of the hearing protector.

In yet a further embodiment, the mounting ring and the cushion of the hearing protector are retained with each other, preferably by a third and fourth retention structure corresponding to each other. For example, a retention structure may be provided as a connection means in the form of a thread or any other suitable connection means. Such an arrangement provides for an easy and reliable attachment of the sensor module to the cup and the cushion, respectively, of the hearing protector.

In still a further embodiment, the sensor module of the hearing protector further comprises a power supply for electrically powering the sensor module. Such a power supply arranged in the sensor module provides for a compact design of the sensor module with all required functions and components and enables the sensor module to work independently from the power supply of the hearing protector thereby saving the energy thereof.

In one embodiment, the sensor module of the hearing protector further comprises a memory for storing data generated by the cushion sensor and/or the module sensor. Such a memory built into the sensor module helps with data processing and storage. Furthermore, there is no need to access memory of the hearing protector so that the sensor module can store sensor data independently of the hearing protector thereby saving memory capabilities thereon.

In another embodiment, the cushion sensor of the hearing protector comprises a skin sensor. Such skin sensor may, e.g. be able to sense skin data such as skin temperature, skin resistance and other relevant data of the user's or wearer's skin. Such skin sensors are advantageous as skin data can easily be sensed and further processed thereby.

In yet another embodiment, the cushion sensor of the hearing protector comprises a physiological sensor, wherein the physiological sensor is configured to generate signal data associated with one or more physiological parameters of the user. Preferably, the cushion comprises a ventilation passage extending entirely through the cushion, wherein the physiological sensor is preferably disposed within the ventilation passage. Such a physiological sensor is advantageous as the physiological parameters of a user or wearer can easily and reliably be detected and further processed thereby.

In still another embodiment, the physiological parameters comprise heart rate, blood oxygen (PPG), temperature, heat flux, biopotentials (EEG, ECG). The detection of such physiological parameters is useful in order to determine the physiological condition of a user or wearer of a hearing protector according to the present disclosure.

In yet another embodiment, the hearing protector further comprises a cup sensor being configured to generate signal data associated with temperature, humidity and/or sound. The cup sensor is connected to the sensor module. Optionally, the cup sensor is spring-mounted to the sensor module or to the earmuff. In other words, the cup sensor is located in the cup or in the sensor module and is for configured to sense cup conditions. The advantage of such a cup sensor is that conditions of the cup can easily and reliable be sensed and further processed.

In still another embodiment, the module sensor of the hearing protector comprises an environmental sensor being configured to generate signal data associated with environmental parameters, wherein the environmental parameters comprise ambient temperature, ambient pressure, ambient humidity, ingredients of the ambient atmosphere, sound or noise data. Such an environmental sensor helps to detect ambient conditions of the user or wearer which may influence the working ability of the user or wearer.

In one embodiment, the sensor module of the hearing protector comprises skin sensor contacts for connecting the skin sensor to the sensor module. Such sensor contact represents an easy and reliable way of contacting the sensors when attaching the sensor module to the cushion and the cup, respectively, of the hearing protector.

In a further embodiment, the sensor module of the hearing protector further comprises an active communication device comprising a loudspeaker and electronic circuitry which comprises a wireless communication interface, the electronic circuitry being configured to drive the loudspeaker based on information received via the wireless communication interface. Such an active communication device is useful as it enables the user or wearer of such a hearing protector to communicate with others in the surrounding even without taking off the hearing protector. Thereby, a risk of taking off the hearing protector because of the need to communicate in a noisy environment is reduced or avoided.

In a certain embodiment, the active communication device of the hearing protector comprises a microphone, wherein the microphone and the electronic circuitry being connected or connectable such that the electronic circuitry can receive information from the microphone and transmit the information via the wireless communication interface. Such a microphone enables a good voice communication of the user or wearer with others in the surrounding. Optionally, the microphone further comprises an accelerometer. Such an accelerometer is useful to provide movement information about the user or wearer of such a hearing protector.

In one embodiment, the hearing protector comprises at least one microphone configured to obtain noise information about the surrounding of the user of the hearing protector. The ambient microphone may be useful for an active noise cancellation in order to provide the required noise information from the surrounding. Additionally, the hearing protector may comprise one or more microphones located within the cup or cushion configured to obtain sound information from within the cup or cushion. Such sound information may—together with the sound information of the surrounding—be used to provide for a fit check, i. e. to check how tight the seal between the cushion and the user's skin is. This is useful as it ensures a good fit of the hearing protector.

In a certain embodiment, the microphone of the hearing protector is a bone-conducting microphone. Such a bone-conducting microphone provides for a reliable voice transmission of the user or wearer even under noisy conditions.

In another embodiment, the hearing protector further comprises a headband for retaining the earmuffs in position, wherein the earmuffs are pivotally connected with their cup to the headband. Such a headband is useful to provide correct positioning of the earmuffs of the hearing protector onto the user's or wearer's ears.

In a further embodiment, the hearing protector further comprises mounting means for mounting each of the earmuff to the lateral sides of a protective helmet. Such mounting means are useful if the hearing protector is used with other personal protective equipment such as a protective helmet. An easy and reliable attachment of the hearing protector to a protective helmet is achieved thereby maintaining a correct position of the earmuffs even when wearing such a helmet.

In one embodiment of the method of retrofitting, the cushion of the hearing protector is molded. The advantage of such a molded cushion is that an easy and reliable manufacturing of the cushion is achieved thereby. In particular, forming openings and/or passages through the cushion can easily and reliably be achieved by a molding process. Suitable molding processes include injection molding, in particular a two shot-injection molding process which even allows to form more than one component at a time, if required.

In another embodiment of the method of retrofitting, the sensor module of the hearing protector further comprises a processing unit for processing a sensor signal from the module sensor and/or from the cushion sensor. The advantage of such a processing unit in the sensor module is that the processing occurs closely located to the sensors of the sensor module. Also, a compact design with the required functionality of the sensor module is achieved thereby. Also, the processing unit may be used to process the sensor signals for signal fusion and further predictive processing of a health state of the headset wearer.

In a further embodiment of the method of retrofitting, the sensor module of the hearing protector further comprises a mounting ring wherein the mounting ring has a first retention structure, and wherein the sensor module is attached to the cup by a first retention structure being retained with a corresponding retention structure at the cup. Such a retention structure provides for an easy and reliable attachment of the sensor module to the cup and the cushion, respectively, of the hearing protector.

In yet a further embodiment of the method of retrofitting, the sensor module of the hearing protector is attached to the cushion such that the mounting ring and the cushion are retained with each other (by a third and fourth retention structure corresponding to each other). Such an arrangement provides for an easy and reliable attachment of the sensor module to the cup and the cushion, respectively, of the hearing protector.

In still a further embodiment of the method of retrofitting, the cushion of the hearing protector further comprises at least one opening. Such openings may go through the cushion material such that passages through the cushion are formed thereby. The advantage of such a molded cushion is that an easy and reliable manufacturing of the cushion is achieved thereby. In particular, forming openings and/or passages through the cushion can easily and reliably be achieved by a molding process. Suitable molding processes include injection molding, in particular a two shot-injection molding process which even allows to form more than one component at a time, if required. The advantage of openings and passages through the cushion is that these provide access to a cushion sensor, which is located within the cushion.

In another embodiment, the hearing protector comprises further sensors for sensing movement of a user or wearer. For example, a movement sensor or an accelerometer may be arranged at the hearing protector to detect such user movement. It is also conceivable to arrange a gyro meter at the hearing protector in order to detect specific movement of the user or wearer, e. g. a circular movement. Such further sensors may help to increase the sensing of the conditions in which the wearer or user of the hearing protector is.

A hearing protector according to the present disclosure may be made by arranging the sensor module, the required sensors and/or electronic components onto one or more printed circuit boards (PCB) and to arrange these PCB's at the hearing protector or more specifically within one or both cups of the hearing protector. It is also conceivable, that other parts, e. g. a headband, if present, contains sensors or other electronic components. One way of providing a hearing protector according to the present disclosure is provided by the method of retrofitting a conventional hearing protection with a sensor module as described above.

The invention was described in various embodiments above. It is understood by a person skilled in the art, that one of, several of or all the above-mentioned embodiments can be combined with each other.

The invention will now be described in more detail with reference to the following Figures exemplifying particular embodiments of the invention:

BRIEF DESCRIPTION OF THE FIGURES

FIG. 1 shows in a schematic functional top view the hearing protector 10 according to an embodiment of the present disclosure comprising a sensor module 30. The sensor module comprises a module sensor 32, a processing unit 34 for processing sensor data and/or for processing data externally received, a memory 36 for storing sensor data and/or external data and a power supply 38 for powering the components of the sensor module 30. The power supply 38 may also power further components of the hearing protector 10. The hearing protector 10 further comprises an earmuff 12, 14 (only one of which is shown here) with a cup sensor 43 and a cushion 22, 24 (only one of which is shown here) with a cushion sensor 42. As indicated, the cup sensor 43 and the cushion sensor 42 are connected to the sensor module 30. The hearing protector 10 further comprises an external sensor 44 which is also connected to the sensor module 30. Furthermore, in some embodiments, the hearing protector 10 may comprise an active communication unit 50 to enable the user (not shown here) of the hearing protector 10 to communicate with others in the surrounding without the need to take off the hearing protector 10 when communicating is needed. The active communication unit 50 further comprises a loudspeaker 52 for playing a sound to the user of the hearing protector 10 and electronic circuitry 54 for processing communication signals of the active communication unit 50. The active communication unit 50 comprises a wireless communication unit 56 and an antenna 72 for wirelessly transmitting communication signals to other users and/or devices (not shown here). Also, the active communication unit 50 is connected to the sensor module 30, e. g. for transferring sensor data from the sensor module to other devices or to transfer external data to the sensor module 30. The active communication unit may also comprise a microphone 74 mounted to a microphone boom 70 (not shown here, please see FIG. 2).

FIG. 2 shows in a schematic front view the hearing protector 10 according to an embodiment of the present disclosure worn by a user 100. The hearing protector 10 comprises the same functional components as illustrated above in FIG. 1. As can be seen from FIG. 2, the hearing protector 10 comprises two earmuffs 12, 14 each having an cup 12A, 14A. Attached to each of the earmuffs 12, 14 are cushions 22, 24 to contact the skin of the user 100 for providing a tight seal against the environment of the hearing protector 10, e. g. against ambient noise. Each of the earmuffs 12, 14 is mounted to a headband 16 by earmuff mounts 18, 20 engaging earmuff mounts of the headband and with the earmuff extensions 26, 28 of the headband 16, respectively, which keep the earmuffs 12, 14 connected to the headband in a pivoting relation to adapt to the user's skin. Similar to FIG. 1, the cup 12A of the hearing protector 10 comprises the sensor module 30, which is in the embodiment shown mounted on one of the cups 12A only. It is conceivable that both cups 12A, 12B have a sensor module 30 mounted thereon. The hearing protector 10 further comprises a microphone 74 mounted to one of the earmuffs 14 by a microphone boom 70. The microphone 74 enables the user 100 to send voice signals for communication to other users in the surrounding.

Figure 1:
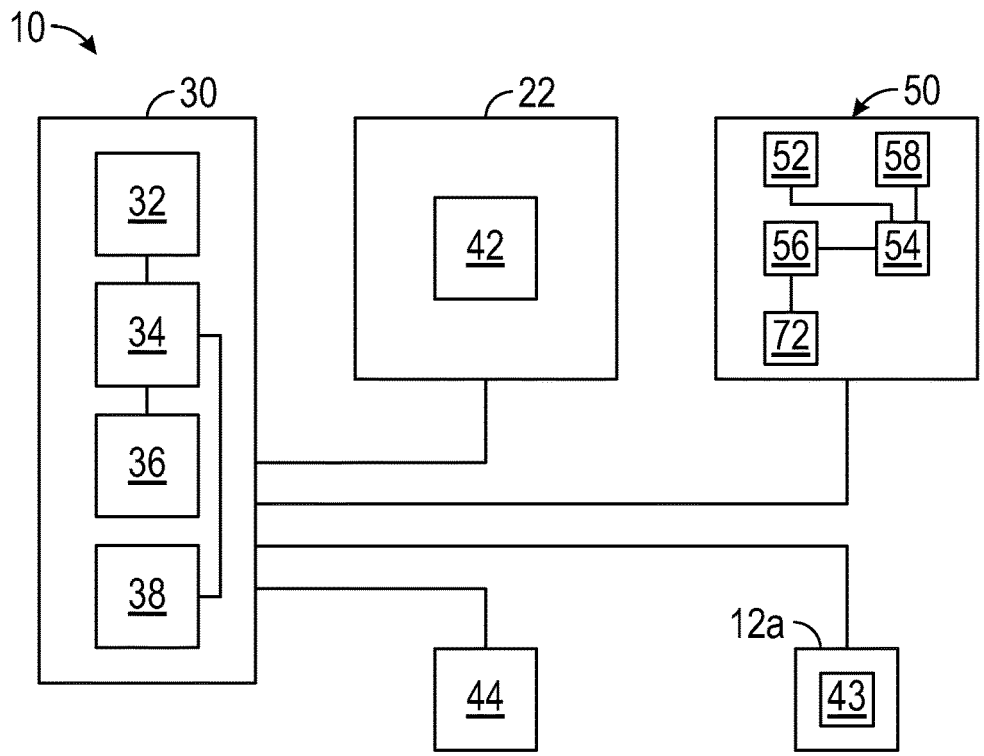
FIG. 1 is a schematic functional top view of the hearing protector according to an embodiment of the present disclosure.
Figure 2:
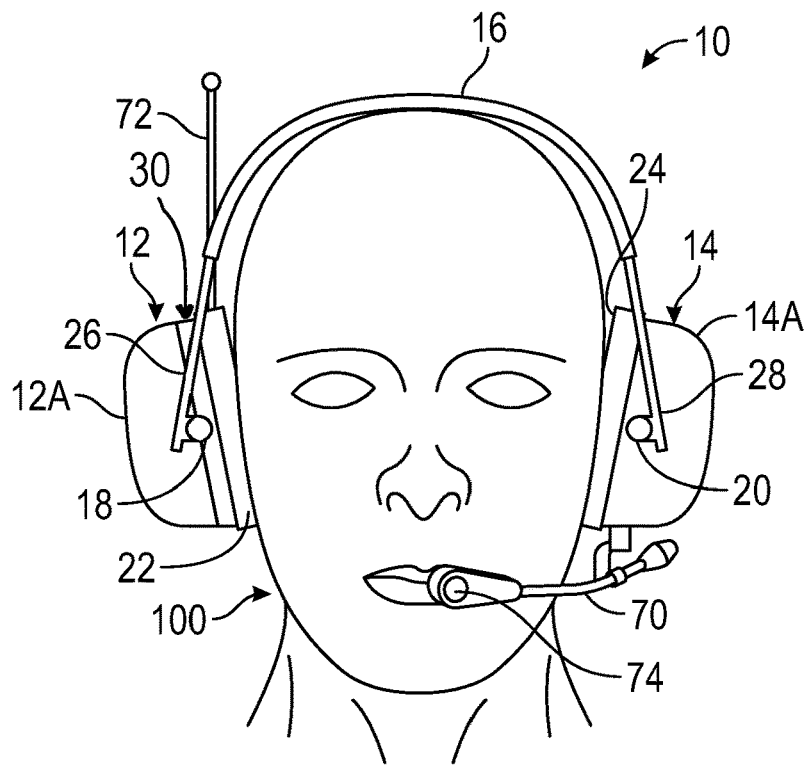
FIG. 2 is a schematic front view of the hearing protector according to an embodiment of the present disclosure worn by a user.
Figure 3:
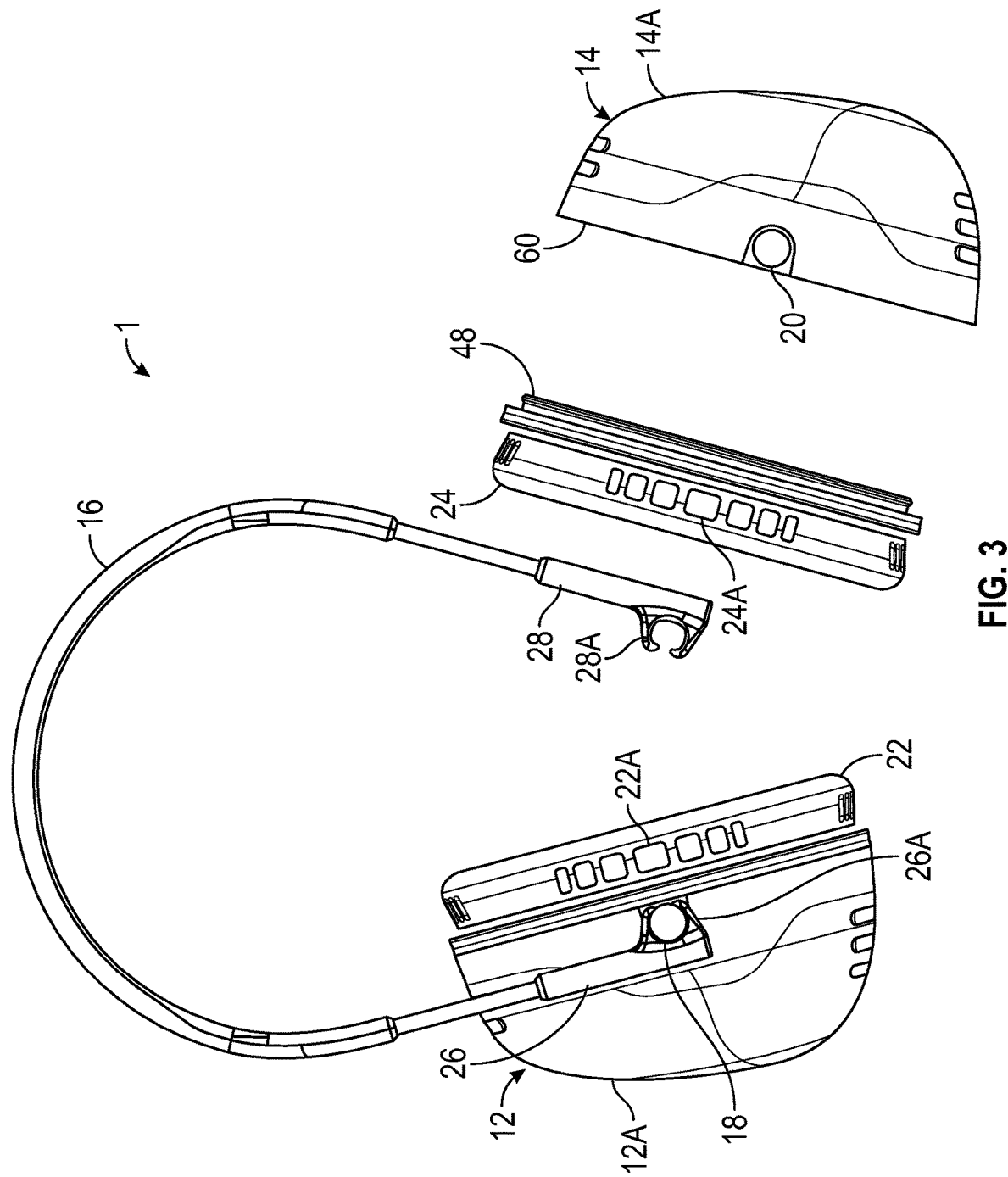
FIG. 3 is a partially exploded front view of a hearing protector according to the prior art, wherein the cushion has been detached from the cup.
Figure 4:
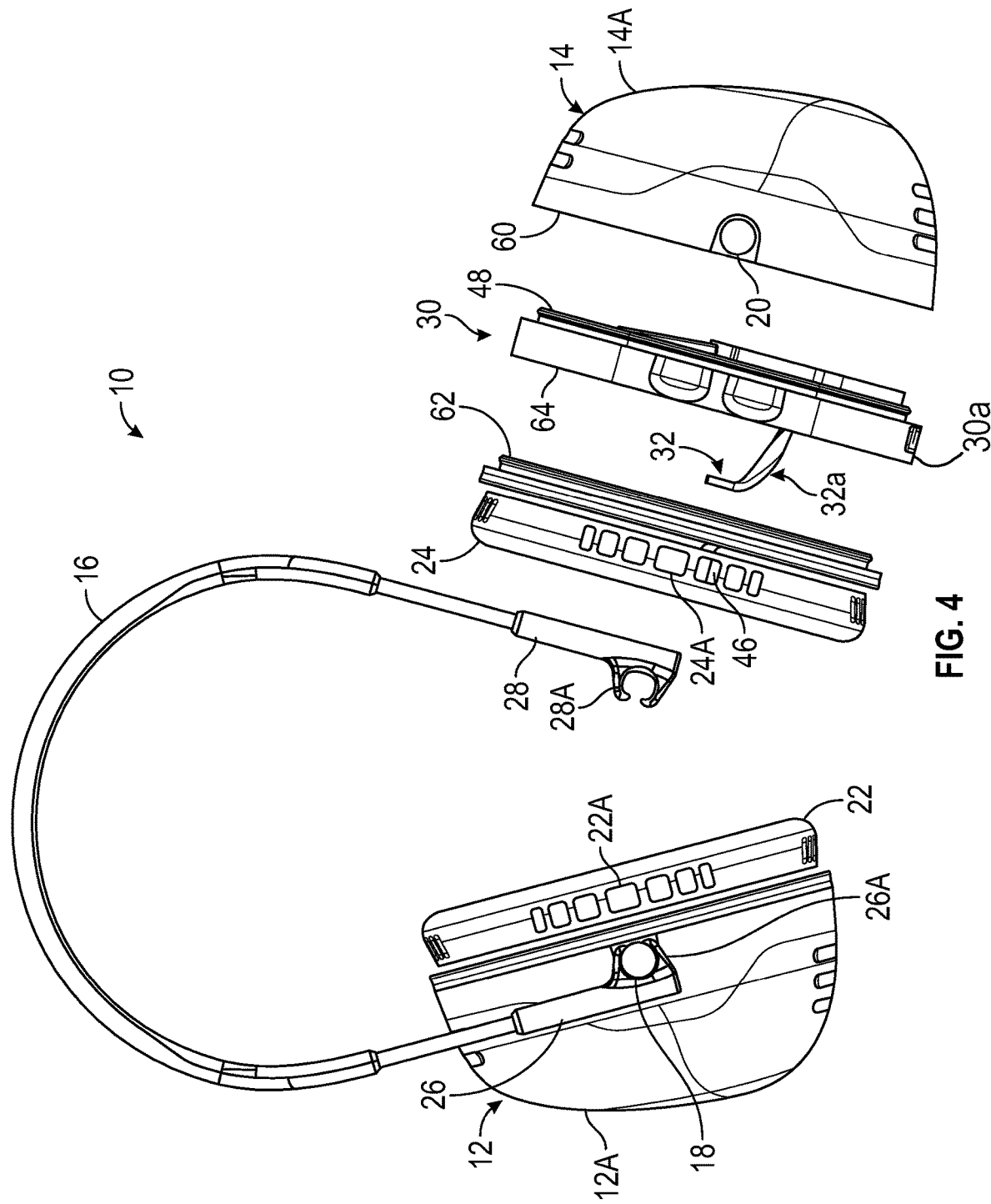
FIG. 4 is a partially exploded front view of a hearing protector according to an embodiment of the present disclosure, wherein the cushion is still detached from the cup and wherein a sensor module according to the present disclosure has been placed between the cushion and the cup.

FIGS. 3 and 4 each show in a schematic front view an embodiment of the hearing protector 10, wherein FIG. 3 shows a conventional hearing protection device 1 according to the prior art and wherein FIG. 4 shows the hearing protector 10 which has been arranged with, preferably been retrofitted with a sensor module 30 according to an embodiment of the present disclosure. FIG. 3 illustrates the method of retrofitting of a conventional hearing protection device 1, wherein the cushion 24 has been detached from the cup 14A of the earmuff 14. The cushion 24 of the hearing protector 1 comprises openings 24A disposed thereon. It is to be noted that in the embodiment shown, the earmuff mount 28A of the headband 16 has been disconnected from the earmuff mount 20 of the earmuff 14 to allow for more space of working. In this spaced-apart configuration, the retention structure or connection means 48 of the cushion 24 and the retention structure or connection means 60 of the cup 14A have been disconnected from each other. Although earmuff 14 has been disconnected from the headband 16 by disconnecting the earmuff mount 28A of the headband 16 from the earmuff mount 20 of the earmuff 14, this step may be omitted depending on the dimension, the available space and the skills of the person carrying out the retrofitting method. The other earmuff 12 of the hearing protector 1 is still shown in its original configuration having the cushion 22 attached to the cup 12A of the earmuff 12. Here, the earmuff 12 is still connected to the headband 16. FIG. 4 illustrates the further steps of the method of retrofitting the hearing protector 10. The sensor module 30 contained in a mounting ring is placed between the cushion 24 and the cup 14A of the earmuff 14 being in a spaced-apart configuration as provided by the step described above. The cushion 24 of the hearing protector 10 being retrofitted comprises openings 24A disposed thereon. In a next step, the retention structures or connection means 48, 64 of the mounting ring 30A containing the sensor module 30 will be each connected to the retention structure or connection means 60 of the cup 14A and to the retention structure or connection means 62 of the cushion 24. In case that the earmuff 14 had been disconnected from the headband 16, the earmuff 14 needs to be re-connected thereto. In the embodiment shown, the module sensor 32 is mounted on a spring 32A. The method of retrofitting has been illustrated for one earmuff 14 only for the reason of simplification of FIGS. 3 and 4. It is understood by the skilled person that similar steps are being carried out to complete the method of retrofitting the hearing protector 10 for the other earmuff 12 as well if retrofitting of both earmuffs is desired. However, it is also conceivable that only one earmuff 14 is retrofitted with a sensor module and a mounting ring, respectively, and the other earmuff 12 remains in its original configuration.

Figure 5:
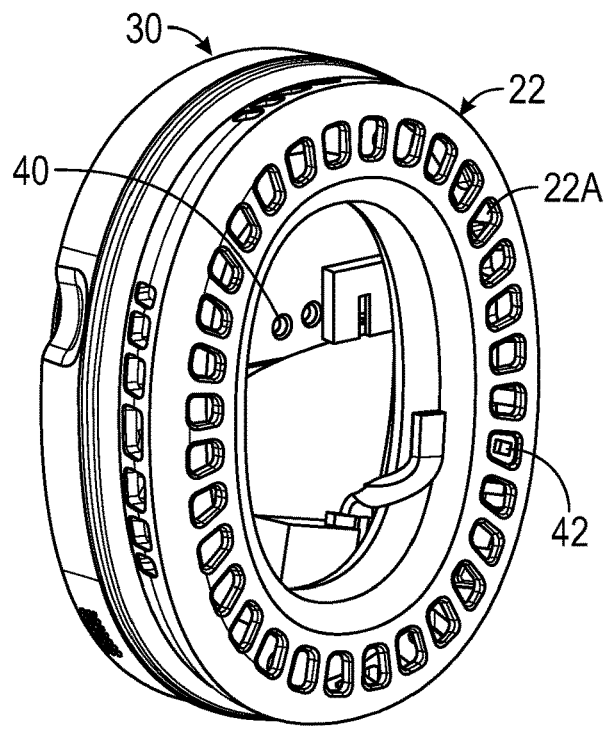
FIG. 5 is a perspective schematic view of the cushion with the sensor module attached thereto according to an embodiment of the present disclosure.

FIG. 5 shows in a perspective schematic view the cushion 22 with the sensor module 30 attached thereto according to an embodiment of the present disclosure. In this view, the cup 12A of the earmuff 12 has been omitted for simplification. As can be seen, the cushion 22 comprises openings or passages therethrough as indicated with 22A. Openings or passages 22A allow for access of the ambient air to the interior of the cushion 22, thereby allowing a sensor mounted to the cushion 22 to be accessed from the outside. This may increase the sensing accuracy of a sensor 42 mounted to the cushion 22. As can be further seen from FIG. 5, cup sensor 43 (not visible here) is arranged in cup 12A of the earmuff 12 of the hearing protector 10 such that it is in close contact to the openings 40, which allow access to the cup sensor 43 (not visible here) from this side similarly as the access is provided for the cushion sensor 42.

Figure 6:
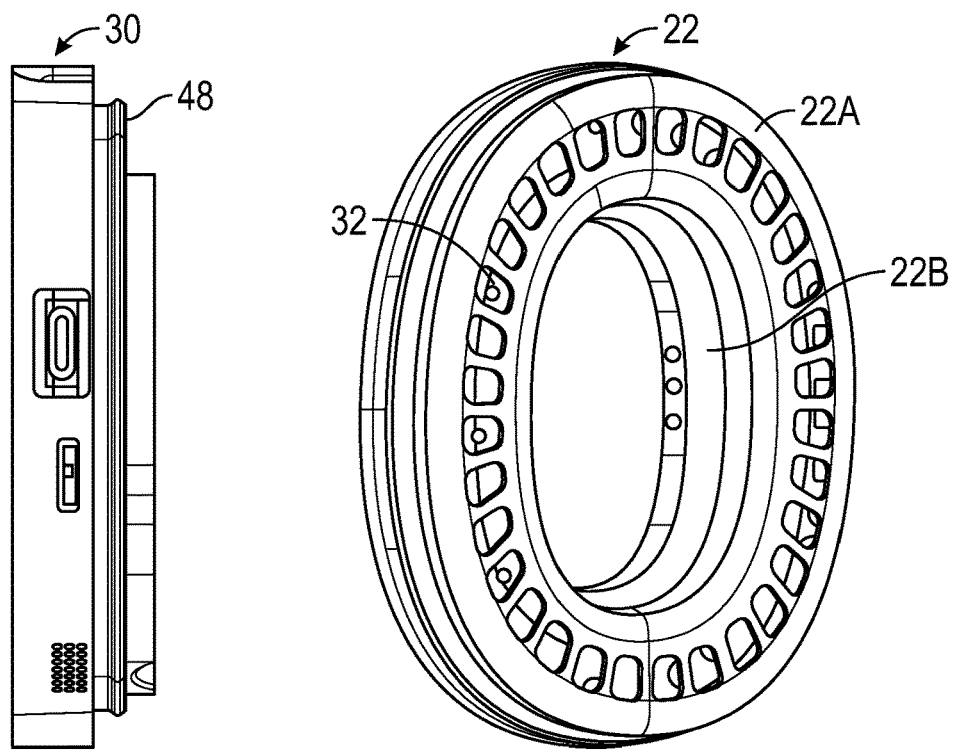
FIG. 6 is a perspective schematic view of the cushion and the sensor module according to an embodiment of the present disclosure before attachment to each other.

FIG. 6 shows in a perspective schematic view the cushion 22 and the sensor module 30 according to an embodiment of hearing protector 10 according to the present disclosure before attachment to each other. The sensor module 30 is similar to the one shown above. In the figure, connection means 48 of the ring-shaped sensor module 30 is still exposed, i. e. not connected to the respective connection means (not visible here) of the cushion 22. FIG. 6 further shows a large oval opening 22B of the cushion 22, which is foreseen to house the user's ear (not shown here). The cushion 22, similarly to the embodiment as shown in FIG. 5, also comprises openings or passages 22A therethrough to allow for access of a cushion sensor 42.

The invention claimed is:

1. A hearing protector comprising two earmuffs, each earmuff having a first side facing—in use—towards an ear of a user (100) and a second side opposite to each other, wherein the earmuffs each comprise:
 a. a cup comprising a first side and a second side each opposite to each other,
 b. a cushion comprising
   i. a first side;
   ii. a second side opposite to each other; and,
   iii. at least one cushion sensor,
 wherein at least one of the earmuffs further comprises:
 c. a sensor module comprising
   i. a first side;
   ii. a second side opposite to each other; and,
   iii. at least one module sensor,
 wherein the sensor module is removably attached with its second side to the first side of the cup,
 wherein the sensor module is removably attached with its first side to the second side of the cushion; and,
 wherein the sensor module is connected to the at least one cushion sensor.

2. The hearing protector according to claim 1, wherein the sensor module further comprises a processing unit for processing a sensor signal from the module sensor and/or from the cushion sensor.

3. The hearing protector according to claim 1, wherein the cushion is molded, wherein the cushion optionally comprises at least one opening.

4. The hearing protector according to claim 1, wherein the sensor module is ring-shaped.

5. The hearing protector according to claim 1, wherein the sensor module comprises a mounting ring being shaped and sized essentially in accordance to the shape and size of the cushion, wherein the mounting ring is adapted for carrying the cushion.

6. The hearing protector according to claim 5, wherein the mounting ring has a first retention structure being retained with a corresponding second retention structure at the cup.

7. The hearing protector according to claim 5, wherein the mounting ring and the cushion are retained with each other preferably by a third and fourth retention structure corresponding to each other.

8. The hearing protector according to claim 1, wherein the cushion sensor comprises a skin sensor.

9. The hearing protector according to claim 1, wherein the cushion sensor comprises a physiological sensor, wherein the physiological sensor is configured to generate signal data associated with one or more physiological parameters of the user, wherein the cushion preferably comprises a ventilation passage extending entirely through the cushion, wherein the physiological sensor is preferably disposed within the ventilation passage.

10. The hearing protector according to claim 1, wherein the physiological parameters comprise heart rate, blood oxygen (PPG), temperature, heat flux, biopotentials (EEG, ECG).

11. The hearing protector according to claim 1, further comprising a cup sensor being configured to generate signal data associated with temperature, humidity and/or sound, wherein the cup sensor is connected to the sensor module and wherein the cup sensor is optionally spring-mounted to the sensor module or to the earmuff.

12. The hearing protector according to claim 1, wherein the module sensor comprises an environmental sensor being configured to generate signal data associated with environmental parameters, wherein the environmental parameters comprise ambient temperature, ambient pressure, ambient humidity, ingredients of the ambient atmosphere, sound or noise data.

13. The hearing protector of claim 1, wherein the sensor module further comprises an active communication device comprising a loudspeaker and electronic circuitry which comprises a wireless communication interface, the electronic circuitry being configured to drive the loudspeaker based on information received via the wireless communication interface.

14. The hearing protector according to claim 13, wherein the active communication device comprises a microphone, wherein the microphone and the electronic circuitry being connected or connectable such that the electronic circuitry can receive information from the microphone and transmit the information via the wireless communication interface, wherein the microphone optionally further comprises an accelerometer.

15. Method of retrofitting a hearing protector with a sensor module according to claim 1, the method comprising the steps of:
- providing a hearing protector comprising two earmuffs, each earmuff having a first side facing—in use—towards an ear of a user and a second side opposite to each other, wherein the earmuffs each comprise a cup comprising a first side and a second side opposite to each other and a cushion comprising a first side and a second side opposite to each other and at least one cushion sensor;
- providing a sensor module comprising a first side and a second side opposite to each other and at least one module sensor, wherein the sensor module is configured to be removably attached with its second side to the first side of the cup, wherein the sensor module is configured to be removably attached with its first side to the second side of the cushion and wherein the sensor module is configured to be connected to the at least one cushion sensor;
- detaching the cushion from the cup;
- attaching the sensor module with its second side to the first side of the cup; and,
- attaching the sensor module (30) with its first side to the second side of the cushion (22, 24).

* * * * *